United States Patent [19]

Rosenberg

[11] Patent Number: 5,797,744
[45] Date of Patent: Aug. 25, 1998

[54] DENTAL PROPHY CUP HAVING A MICROCELLULAR POLISHING SURFACE AND METHOD OF MAKING

[75] Inventor: Neil A. Rosenberg, Nantucket, Mass.

[73] Assignee: NAR Inc., Barrington, R.I.

[21] Appl. No.: 757,636

[22] Filed: Dec. 2, 1996

[51] Int. Cl.$^6$ .................................................. A61C 3/06
[52] U.S. Cl. ........................................................ 433/166
[58] Field of Search ................................ 433/166, 165

[56] References Cited

U.S. PATENT DOCUMENTS

| 387,581 | 8/1888 | Custer | 433/166 |
|---|---|---|---|
| 1,644,465 | 10/1927 | Chott | 433/166 |
| 4,259,071 | 3/1981 | Warden et al. | 433/166 |
| 5,078,754 | 1/1992 | Jefferies et al. | 51/298 |
| 5,083,922 | 1/1992 | Yale | 433/166 |
| 5,316,475 | 5/1994 | Rosenberg | 433/166 |
| 5,360,339 | 11/1994 | Rosenberg | 433/166 |
| 5,369,916 | 12/1994 | Jefferies et al. | 451/532 |
| 5,405,265 | 4/1995 | Mendoza | 433/166 |

*Primary Examiner*—John J. Wilson
*Attorney, Agent, or Firm*—Burns, Doane, Swecker & Mathis, LLP

[57] ABSTRACT

A dental prophy cup includes a polishing surface formed by a plurality of annular ridges spaced along a longitudinal axis of rotation of the prophy cup. Each ridge includes a generally forwardly facing side which has a micro-cellular texturing capable of retaining abrasive paste. The cup is molded of a solid elastomeric material in a mold which forms the micro-cellular texturing on the polishing surface.

8 Claims, 2 Drawing Sheets

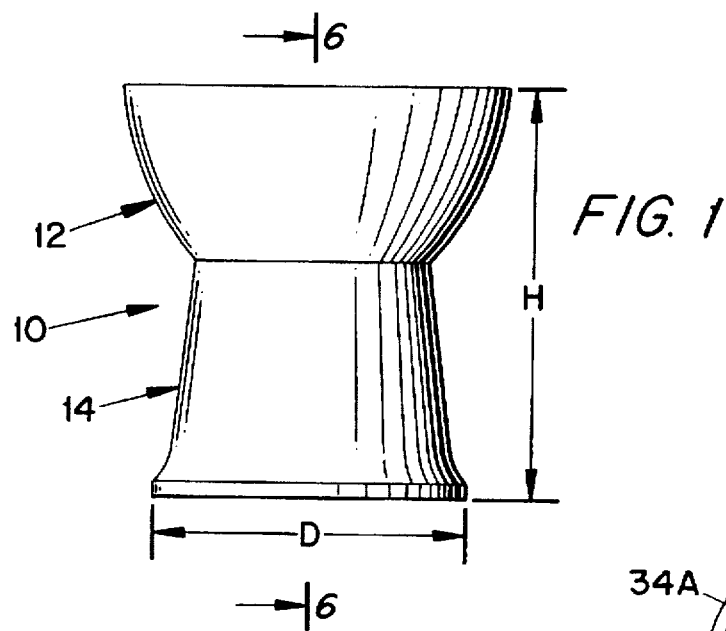
FIG. 1
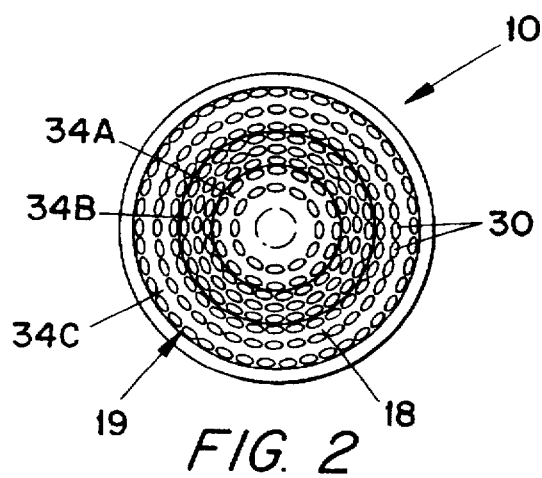
FIG. 2
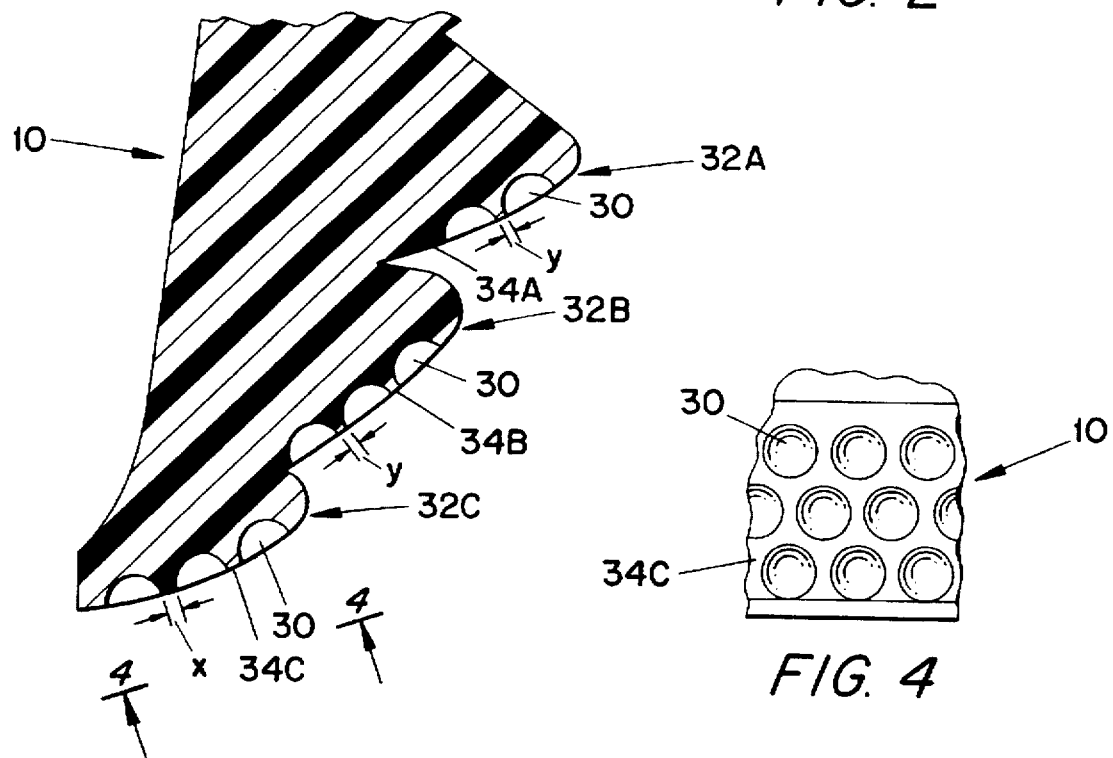
FIG. 3
FIG. 4

1

DENTAL PROPHY CUP HAVING A MICROCELLULAR POLISHING SURFACE AND METHOD OF MAKING

BACKGROUND OF THE INVENTION

The present invention relates to a dental prophy cup used in dental prophylaxis procedures and, in particular, to a novel configuration and construction of such a cup, as well as to a method of making a dental prophy cup.

A dental prophylaxis procedure typically involves the application of an abrasive paste (i.e., a paste containing abrasive particles) to a tooth surface upon which pressure and rotational motion are applied. The removal of plaque, calculus and stains is facilitated by the resultant abrasion at the interface between the abrasive particles and tooth surface.

The pressure and rotational motion are applied to the abrasive paste by means of a prophy cup which comprises an elastic cup-shaped element of about one-quarter inch diameter. A rear portion of the cup is mounted on a drive shaft which rotates the cup at high speed, e.g., about 1500 rpm. The front portion of the cup forms an internal cavity which receives the paste. The wall of the cavity may include a plurality of fins extending in a front-to-rear direction. An operator presses the front portion of the cup against a tooth following the insertion of abrasive paste into the cavity. The paste serves as a lubricant, and the abrasives in the paste function to abrade away plaque, calculus, and stains from the tooth surfaces.

This procedure has traditionally exhibited certain shortcomings. For example, the centrifugal force generated by a prophy cup rotating at 1500 rpm causes the paste to be displaced from the cavity. Since the surface of the cup which engages the tooth is smooth, only minimum resistance to the displacement of the paste is presented. The displacement of paste results in reduced abrasion and cleaning performance.

Also, abrasive particles of the paste disposed between the smooth cup surface and the tooth surface can produce excessive scratching of the tooth surface.

Disclosed in U.S. Pat. Nos. 5,078,754 and 5,369,916 is a dental prophy cup formed of a polyurethane foam wherein the foaming process creates air pockets or voids throughout the foam and at the cup surface. The pockets at the cup surface would inherently form a texturing capable of retaining abrasive paste, and more effectively resisting outward displacement of the paste better than a smooth surface. However, due to the presence of air pockets throughout the foam, the cup would not be firm enough, i.e., it would be too pliable to transmit sufficient pressure to the teeth.

Therefore, it would be desirable to provide a dental prophy cup which increases the residence time of abrasive paste therein, while being capable of transmitting sufficient pressure to the teeth, without producing excessive scratching of the teeth.

SUMMARY OF THE INVENTION

These and other objects are achieved by the present invention which relates to a dental prophy cup comprising a body having a rear mounting portion and a front polishing portion formed of one piece with the mounting portion. The mounting portion is adapted to be mounted on a handpiece for rotation about a longitudinal center axis of the body. The polishing portion includes a front surface forming a forwardly open center cavity for receiving abrasive paste. The body is formed of a solid elastomeric material, whereby the polishing portion is elastically flexible in response to being pressed against a tooth to enable the front surface to generally conform to a contour of the tooth. The front surface possesses a micro-cellular structure for retaining abrasive paste during a tooth-polishing operation.

Preferably, the micro-cellular texture of the front surface is defined by generally semi-spherical cells, each cell having a radius in the range of about 80 to 300 microns.

The front is surface preferably comprised of a plurality of annular ridges spaced along the center axis. The ridges are of progressively larger radius toward a front end of the cavity. Each ridge includes a generally forwardly facing side possessing the micro-cellular texturing.

BRIEF DESCRIPTION OF THE DRAWING

The objects and advantages of the invention will become apparent from the following detailed description of preferred embodiments thereof in connection with the accompanying drawing in which like numerals designate like elements and in which:

FIG. 1 is a side elevational view of a dental prophy cup according to the present invention;

FIG. 2 is a front end view of the prophy cup depicted in FIG. 1;

FIG. 3 is an enlarged fragmentary view of a portion of the prophy cup depicted in FIG. 1;

FIG. 4 is a fragmentary view of the prophy cup viewed in the direction of line 4—4 in FIG. 3;

DETAILED DESCRIPTION OF A PREFERRED EMBODIMENT OF THE INVENTION

Figure 5:
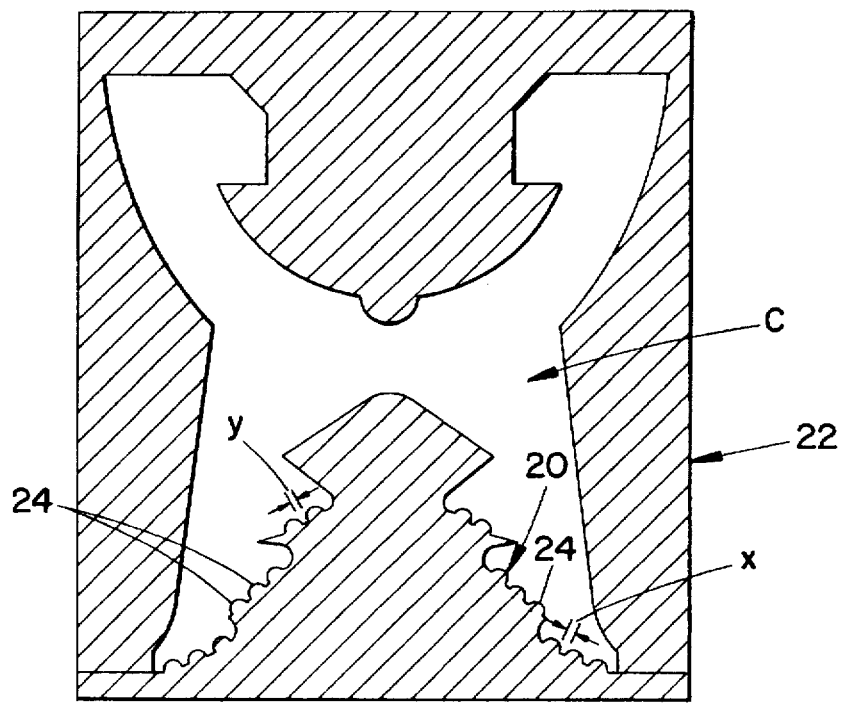
FIG. 5 is a longitudinal sectional view taken through a mold for forming the prophy cup depicted in FIG. 1.
Figure 6:
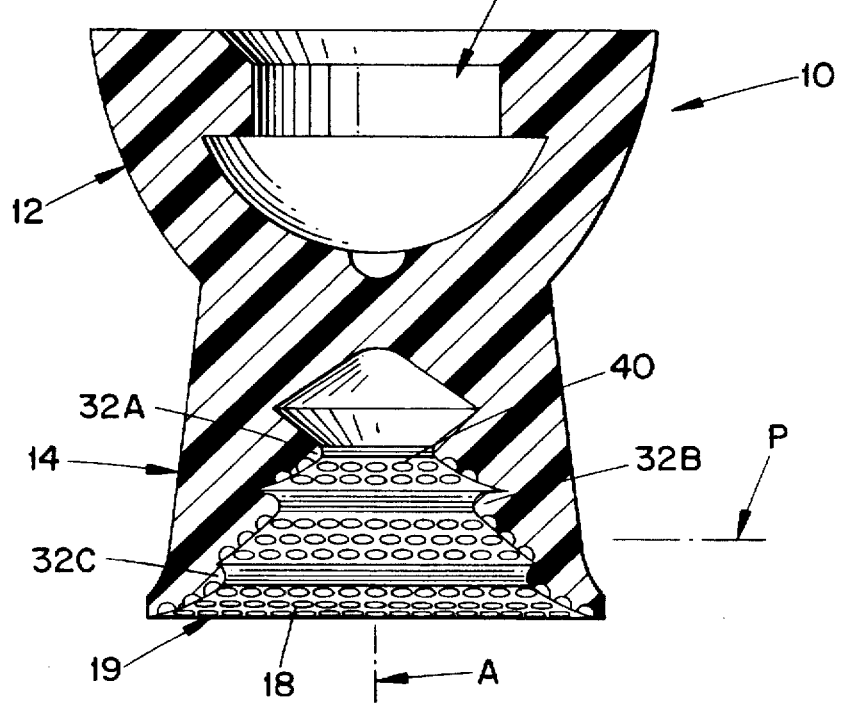
FIG. 6 is a longitudinal sectional view taken along the line 6—6 in FIG. 1.

Depicted in FIGS. 1–4 and 6 is a dental prophy cup comprising a body 10 having a rear mounting portion 12 and a front polishing portion 14. The mounting portion includes a recess 16 adapted to be attached to a conventional handpiece (not shown) for rotation about a longitudinal axis A of the body (see FIG. 6).

The polishing portion 14 includes a front surface 18 forming a forwardly open center cavity 19 for receiving abrasive paste. The body 10 is formed of a solid elastomeric material, preferably polyisoprene having a durometer value of 55–75, so that the polishing portion is elastically flexible in response to being pressed against a tooth, to enable the front surface 18 to flex and generally conform to a contour of the tooth.

The front surface 18 has a microcellular texture so as to be capable of retaining abrasive paste and resist outward displacement thereof. Yet, because the body 10 is formed of a solid elastomeric material instead of, for example, a foamed elastomeric material, the polishing surface is able to transmit sufficient pressure to the tooth surface.

The texturing is formed by microcells of generally semi-spherical shape, although other cell shapes are possible. Alternatively, the microcellular texturing could be formed by tiny, short, spaced-apart fingers (not shown) which project forwardly from the front surface.

The cup is made by a flashless molding process in which a face 20 of a mold 22 which forms the microcellular textured tooth engaging surface of the cup is itself textured as shown in FIG. 5. That is, the face 20 is provided with generally semi-spherical bumps 24 each having a radius in the range of about 140 microns (0.0055 inch).

The bumps 24 are arranged in annular rows, each row being coaxial with a longitudinal center axis of the mold cavity C. The bumps of each row are spaced apart by about 0.001 to 0.002 inches, although the bumps could instead be arranged in immediate contact with one another. The rows of bumps disposed nearest to the front end of the mold cavity C are spaced apart by a larger distance than are the rows spaced farther from that forward end. For example, the front rows are spaced apart by a distance x of about 0.0030 inch, whereas the remaining rows are spaced apart by distance y of about 0.0020 inch.

When elastomeric material is injected into the mold cavity C and becomes hardened, a cup will be formed wherein the front surface 18 has cells or pores 30 corresponding in size and location to the bumps 24. Thus, the cell 30 are of generally semi-spherical shape, each with a radius is in the range of about 80 to 300 microns, preferably about 140 microns (about 0.0055 inch).

The front surface 18 is comprised of a plurality of annular ridges 32A, 32B, 32C arranged coaxially with respect to the axis A. The ridges are of larger diameter in a direction toward the front end of the cavity 19. Each ridge includes a generally forwardly facing side 34A, 34B, 34C in which the cells 30 are formed in annular rows. Each cell includes an outer edge 40 lying flush with the front surface 18. That is, an imaginary plane (FIG. 6) extending perpendicular to the center axis A intersects the front surface 18 and a plurality of cells disposed therein. The entire portion of the front surface 18 that is intersected by the plane (i.e., the portion of surface 18 extending from one intersected cell to another) is spaced at a constant distance from the center axis (the distance being measured in a direction perpendicular to the axis A). The cells 30 in each row are spaced apart by about 0.001 to 0.002 inch, although if the bumps 24 were in immediate contact with one another, there would be no spacing between the cells. The rows of cells located in the front side 34C of the ridge 32C are spaced apart by the distance x of about 0.0030, whereas the remaining rows of cells in the sides 34A and 34B are spaced apart by the distance y of about 0.0020 inch.

The overall height H of the cup is about 0.3277 inch, and the front diameter D of the polishing portion is about 0.25 inch.

The bumps 24 are preferably formed in the mold face 20 by a conventional photochemical machining process for precision material removal. In that process, resists are used to copy an image from a mask or pattern generator onto the mold surface. The surface is covered by a thin layer of the resist which is a radiation-sensitive material. This material is then selectively exposed to radiation and the image is thus copied into the resist, which is later developed by removing the portions of the resist that were made more soluble when exposed to the radiation (e.g., electron or x-ray irradiation).

Other methods for forming bumps 24 on the mold surface 20 might be practicable, such as flame spraying steel beads onto a smooth mold surface, or possibly by the use of CNS or EDM machining.

In use of the cup, the abrasive paste is inserted into the cavity 19, and the cup is pressed against a tooth surface with sufficient force (e.g., 0.5 lb) to elastically flex the front surface 18 into general conformance with the contour of the tooth surface. As the cup is rotated, the paste produces a polishing action against the tooth surface to remove plaque, calculus, and stains. Any tendency for the paste to be displaced outwardly by centrifugal force is resisted, because the paste is retained in the cells 30 of the front surface 18. Also, abrasive particles disposed within the cells have less of a tendency to excessively scratch the tooth surface as compared to the case where particles are disposed between a smooth (non-textured) cup surface and the tooth surface.

Importantly, since the cup is formed of a solid (non-foamed) elastomeric material, the cup possesses a sufficient modulus of elasticity to transmit the requisite pressure against the tooth surface.

Although the present invention has been described in connection with a preferred embodiment thereof, it will be appreciated by those skill in the art that additions, deletions, modifications, and substitutions not specifically described may be made without departing from the spirit and scope of the invention as defined in the appended claims.

What is claimed:

1. A dental prophy cup comprising a body having a rear mounting portion and a front polishing portion formed of one piece with the mounting portion, the mounting portion adapted to be mounted on a handpiece for rotation about a longitudinal center axis of the body, the polishing portion including a front surface forming a forwardly open center cavity for receiving abrasive paste, the body formed of a solid elastomeric material whereby the polishing portion is elastically flexible in response to being pressed against a tooth, to enable the front surface to generally conform to a contour of the tooth, the front surface possessing a microcellular texture defining open empty microcells for retaining abrasive paste during a tooth-polishing operation, each microcell including an outer edge lying flush with the front surface, whereby an imaginary plane extending perpendicular to the center axis intersects the front surface and a plurality of the microcells disposed therein, the entire intersected front surface being spaced at a constant distance from the center axis.

2. The dental prophy cup according to claim 1 wherein the solid elastic material is polyisoprene.

3. The dental prophy cup according to claim 1 wherein the microcellular texture of the front surface is defined by generally semi-spherical cells.

4. The dental prophy cup according to claim 3 wherein each cell has a radius in the range of about 80 microns to about 300 microns.

5. The dental prophy cup according to claim 4 wherein each of the cells has a radius of about 140 microns.

6. The prophy cup according to claim 1 wherein the front surface is comprised of a plurality of annular ridges spaced along the center axis, the ridges having a progressively larger diameter toward a front end of the cavity, each ridge including a generally forwardly facing side possessing microcellular texturing.

7. The dental prophy cup according to claim 1 wherein the elastomeric material has a durometer value of from about 55 to about 75.

8. A method of making a dental prophy cup comprising a body having a rear mounting portion and a front polishing portion formed of one piece with the mounting portion, the mounting portion adapted to be mounted on a handpiece for rotation about a longitudinal center axis of the body, the polishing portion including a front surface forming a forwardly open center cavity for receiving abrasive paste, the body formed of a solid elastomeric material whereby the polishing portion is elastically flexible in response to being pressed against a tooth, to enable the front surface to generally conform to a contour of the tooth, the front surface possessing a microcellular texture defined by open empty microcells for retaining abrasive paste during a tooth-polishing operation, each microcell including an outer edge lying flush with the front surface, whereby an imaginary plane extending perpendicular to the center axis intersects the front surface and a plurality of the microcells disposed therein, the entire intersected front surface being spaced at a constant distance form the center axis the method comprising the steps of:

A. providing a mold cavity having a mold face for defining the front face of the cup, the mold face including a plurality of projections;

B. introducing the elastomeric material into the mold cavity such that the projections form the microcellular texturing in the solid elastomeric material; and C. allowing the elastomeric material to harden.

* * * * *